United States Patent [19]

Calverley et al.

[11] Patent Number: 5,401,732
[45] Date of Patent: Mar. 28, 1995

[54] VITAMIN D ANALOGUES

[75] Inventors: Martin J. Calverley; Kai Hansen, both of Herlev; Lise Binderup, Tåstrup, all of Denmark

[73] Assignee: Leo Pharmaceutical Products Ltd. A/S Kemiske Fabrik Produkionsaktiese SKAB, Ballerup, Denmark

[21] Appl. No.: 16,186
[22] Filed: Feb. 11, 1993

Related U.S. Application Data

[63] Continuation of Ser. No. 721,562, Aug. 2, 1991, abandoned.

[30] Foreign Application Priority Data

Feb. 23, 1989 [GB] United Kingdom ............... 8904154

[51] Int. Cl.$^6$ ........................................ C07C 401/00
[52] U.S. Cl. .................................... 514/167; 552/653
[58] Field of Search ......................... 552/653; 514/167

[56] References Cited

FOREIGN PATENT DOCUMENTS 0184112 6/1986 European Pat. Off. .

OTHER PUBLICATIONS

Abe, et. al. "Synthetic analogues of vitamin D3 with an oxygen atom in the side chain skeleton" FEB 05407, vol. 226, No. 1, pp. 58–62 (Dec. 1987).
Chemical Pharm. Bull., vol. 34, No. 10, 1986 Eigoro Murayama et al.: "Synthetic Studies of Vitamin D3 Analogues. VIII Synthesis of 22-oxavitamin D3 Analogues." see pp. 4410–4413.
Chemical Abstracts, vol. 108, No. 11, Mar. 1988, Junko et al, "Synthetic Analogs of Vitamin D3 with an oxygen atom in the side chain skeleton." see abstract 8819v, & FEBS Lett. 1987, 226 (1) 58–62.
Chemical Abstracts, vol. 110, No. 2, Jan. 1989, Katsuhito et al.: "Antitumor pharmaceuticals containing 9, 10-seco-5, 7, 10 (19)-pregnatriene derivatives." see abstracts 13599s & Jpn Kokai Tokkyo Koho JP 63107930, May 1988.

Primary Examiner—Johann Richter
Assistant Examiner—Kimberly J. Kestler

[57] ABSTRACT

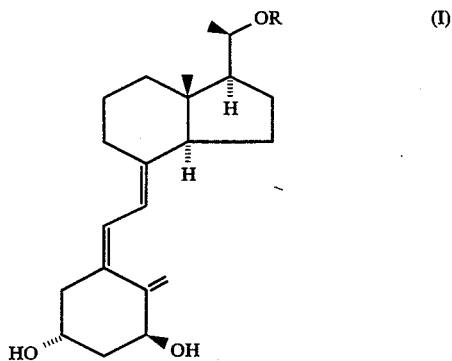

The present invention relates to compounds of formula (I), in which formula R stands for an alkyl group containing from 7 to 12 carbon atoms optionally substituted with a hydroxy group; and derivatives of the compounds of formula (I) in which one or more hydroxy groups have been transformed into —O-acyl or —O-glycosyl or phosphate ester groups, such masked groups being hydrolyzable in vivo, in pure form or in mixtures. The present compounds find use in both the human and veterinary practice in the treatment and prophylaxis of autoimmune diseases, including diabetes mellitus, hypertension, inflammatory diseases such as rheumatoid arthritis and asthma as well as diseases characterized by abnormal cell differentiation and/or cell proliferation, and/or imbalance in the immune system.

7 Claims, No Drawings

VITAMIN D ANALOGUES

This is a continuation of application Ser. No. 07/721,562, filed on Aug. 2, 1991, which was abandoned upon the filing hereof.

This invention relates to a hitherto unknown class of compounds which shows an immunomodulating effect as well as strong activity in inducing differentiation and inhibiting undesirable proliferation of certain cells, including skin cells, to pharmaceutical preparations containing these compounds, to dosage units of such preparations, and to their use in the treatment and prophylaxis of autoimmune diseases, including diabetes mellitus, hypertension, inflammatory diseases such as rheumatoid arthritis and asthma as well as diseases characterized by abnormal cell differentiation and/or cell proliferation, and/or imbalance in the immune system.

The compounds of the present invention are represented by the general formula I

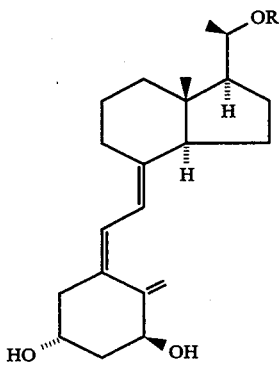

in which formula R stands for an alkyl group containing from 4 to 12 carbon atoms optionally substituted with a hydroxy group.

Preferably R is a group of formula II

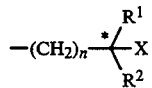

where n is an integer from 1 to 7; $R^1$ and $R^2$, which may be the same or different, stand for hydrogen, lower alkyl, lower cycloalkyl, or, taken together with the carbon atom (starred in formula II) bearing the group X, $R^1$ and $R^2$ can form a $C_3$-$C_8$ carbocyclic ring; X stands for hydrogen or hydroxy.

In the context of this invention, the expression "lower alkyl" indicates a straight or branched saturated or unsaturated carbon chain containing from 1 to 5 carbon atoms, and the expression "lower cyclo-alkyl" indicates a saturated or unsaturated $C_3$-$C_7$ carbocyclic ring.

As can be seen from formula I and II, depending on the meanings of R, X, $R^1$ and $R^2$ the compounds of the invention can comprise several diastereoisomeric forms (e.g. R or S configuration at the starred carbon atom). The invention covers all these diastereoisomers in pure form and also mixtures of diastereoisomers. In addition, derivatives of I in which one or more of the hydroxy groups are masked as groups which can be reconverted to hydroxy groups in vivo are also within the scope of the invention ("bioreversible derivatives or prodrugs of I").

The term "bioreversible derivatives or prodrugs of I" includes, but is not limited to, derivatives of the compounds of formula I in which one or more hydroxy groups have been transformed into —O-acyl or —O-glycosyl groups, or a phosphate ester, such masked groups being hydrolyzable in vivo.

Compounds of formula I in which R is not substituted with hydroxy are another type of prodrug. These compounds are relatively inactive in vitro, but are converted to active compounds of formula I by enzymatic hydroxylation after administration to the patient.

It has recently been shown that $1\alpha,25$-dihydroxyvitamin $D_3$ ($1,25(OH)_2D_3$) influences the effects and/or production of interleukins, indicating the potential use of this compound in the treatment of diseases characterized by a dysfunction of the immune system, e.g. autoimmune diseases and rejection of transplants. In addition, other conditions characterized by an abnormal interleukin-1 production, e.g. inflammatory diseases such as rheumatoid arthritis may be treated with $1,25(OH)_2D_3$.

It has also been shown that $1,25(OH)_2D_3$ is able to stimulate the differentiation of cells and inhibit excessive cell proliferation, and it has been suggested that this compound might be useful in the treatment of diseases characterized by abnormal cell proliferation and/or cell differentiation such as psoriasis.

Also, the use of $1,25(OH)_2D_3$ for the treatment of hypertension and diabetes mellitus has been suggested.

However, the therapeutic possibilities in such indications of $1,25(OH)_2D_3$ are severely limited by the well known potent effect of this hormone on calcium metabolism; elevated blood concentrations will rapidly give rise to hypercalcemia. Thus, this compound and its potent synthetic analogues are not completely satisfatory for use as drugs in the treatment of e.g. psoriasis, or immune diseases which may require continuous administration of the drug in relatively high doses.

A number of oxa-analogues of vitamin $D_3$ are known. $1\alpha,25$-dihydroxy-20-oxa-21-norvitamin $D_3$ and $1\alpha$-hydroxy-20-oxa-21norvitamin $D_3$ are described in N. Kubodera et al, Chem. Pharm. Bull., 34, 2286 (1986), $1\alpha,25$-dihydroxy-22-oxavitamin $D_3$ and 25-hydroxy-22-oxavitamin $D_3$ are described in E. Murayama et al, Chem. Pharm. Bull., 34, 4410 (1986), J. Abe et al, FEBS LETTER, 226, 58 (1987) and European Patent Application, publication number 184 112, and $1\alpha,25$-dihydroxy-23-oxavitamin $D_3$ is described in European Patent Application, publication number 78704.

In vitro experiments indicate that some of these compounds may have advantages over $1,25(OH)_2D_3$. Thus $1\alpha,25$-dihydroxy-22-oxavitamin $D_3$ has only one 14th as much affinity as $1\alpha,25(OH)_2D_3$ for the chick intestinal cytosolic receptor, a weaker affinity than $1,25(OH)_2D_3$ for the receptor in a human myeloid leukemia cell line (HL-60), and a high activity as inducer of differentiation in HL-60 cells.

In contrast to the compounds of the present invention the above mentioned 22-oxa-compounds have the S-configuration in the 20-position.

The usefulness of a vitamin D analogue in the above mentioned indications is dependent not only upon a favourable ratio of binding affinity to relevant receptors compared to the intestinal receptor, but also upon the fate of the compound in the organism.

It has now been found that the compounds of the present invention show favourable selectivity with respect to receptor binding and at the same time show high bioavailability as well as chemical and metabolic stability.

The selectivity of the compounds is illustrated by the fact that while they have high affinities for the receptor in tumour cells (similar to or much better than that of 1,25(OH)$_2$D$_3$) and the concentration needed to induce cell differentiation in a human monocytic tumour cell line is the same as or considerably lower than that needed of 1,25(OH)$_2$D$_3$ to give the same effect, their binding affinity for the intestinal receptor is lower than that of 1,25(OH)$_2$D$_3$. In vivo in rats the compounds are less active than 1,25(OH)$_2$D$_3$ in inducing hypercalciuria and hypercalcemia.

This renders the compounds of the invention especially suited for both local and systemic treatment and prophylaxis of human and veterinary disorders which are characterized by abnormal cell proliferation and/or cell differentiation, such as certain dermatological disorders including psoriasis, leukemia and myelofibrosis, and diseases characterized by an imbalance in the immune system, e.g. autoimmune diseases, and to obtain desired immunesuppression as in transplantation procedures, as well as treatment of acne, diabetes mellitus and hypertension and inflammatory diseases, such as rheumatoid arthritis and asthma. As the compounds of this invention may promote the differentiation of the hair follicle cells, these compounds may be used in the treatment of alopecia.

The compounds of formula I may conveniently be prepared from the vitamin D-derivative 1 (or its 20R isomer) (Tetrahedron, 43, 4609 (1987)) by the routes outlined in Scheme 1. Oxidation of 1 for example using the van Rheenen procedure (Tetrahedron Letters, 1969, 985) gives the ketone 2, which is reduced to the 20R-alcohol 3. When a suitable chiral reducing agent is used 3 may be prepared with very high stereoselectivity, but 3 is conveniently prepared by NaBH$_4$ reduction of 2 and separating the minor amount of corresponding 20S-alcohol chromatographically. O-Alkylation of 3 to give III is achieved by treatment under basic conditions with a side chain building block of general formula Z—R$^3$, in which Z is a leaving group such as a halogen (Cl, Br or I) or p-toluenesulphonyloxy or methanesulphonyloxy, and R$^3$ is R (of formula I) or optionally a radical which can be converted to R at any convenient later stage (or over several stages). Thus R$^3$ in compounds III, IV, V and VI does not necessarily have the same meaning along a particular synthetic sequence. The conversion of R$^3$ to R may well involve several steps and possibly involve a temporary protection of the sensitive triene system of the molecule. Apart from any necessary modification within the side chain (R$^3$), the conversion of III to I involves a photoisomerisation step and a desilylation step, analogous to the steps used in the last stages of the synthesis of other vitamin D analogues (see European patent No. 0 227 826).

The side chain building blocks, R$^3$Z, are either known compounds (several are described in international patent application PCT/DK89/00079) or may be prepared analogously to those described in PCT/DK89/00079. The R$^3$ is typically identical with formula II in which X is a protected OH group, e.g. tetrahydropyranyloxy or trialkylsilyloxy. (Any such THP ethers R$^3$Z, which are not described in PCT/DK89/00079, are readily prepared from the corresponding alcohol).

The following standard abbreviations are used throughout this disclosure: Me=methyl; Et=ethyl; Pr$^n$=n-propyl; Pr$^i$=isopropyl; Bu$^t$=tert-butyl; THP=tetrahydro-4H-pyran-2-yl; THF=tetrahydrofuran: Ts=p-toluenesulphonyl; TBA=tetra-(n-butyl)-ammonium.

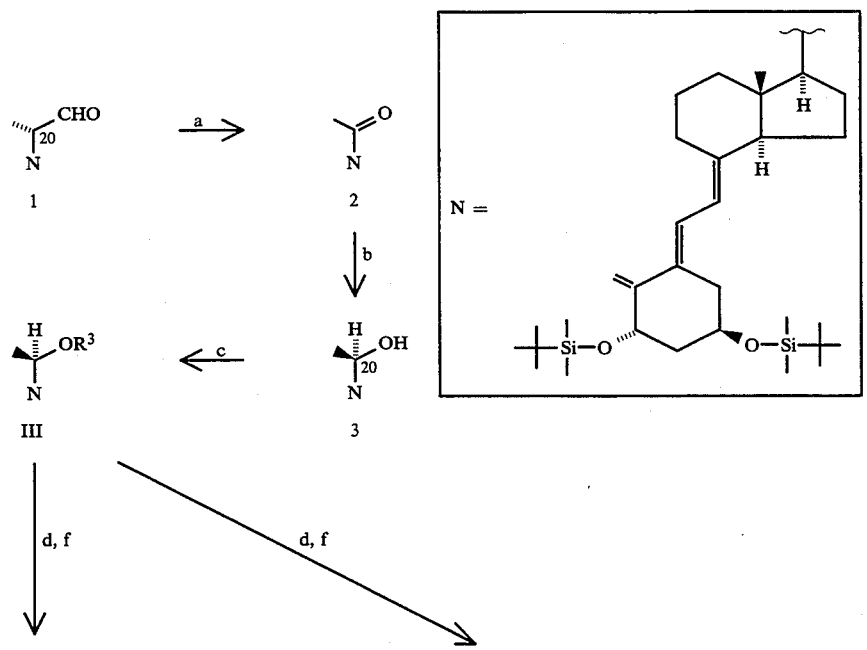

Scheme 1

-continued
Scheme 1

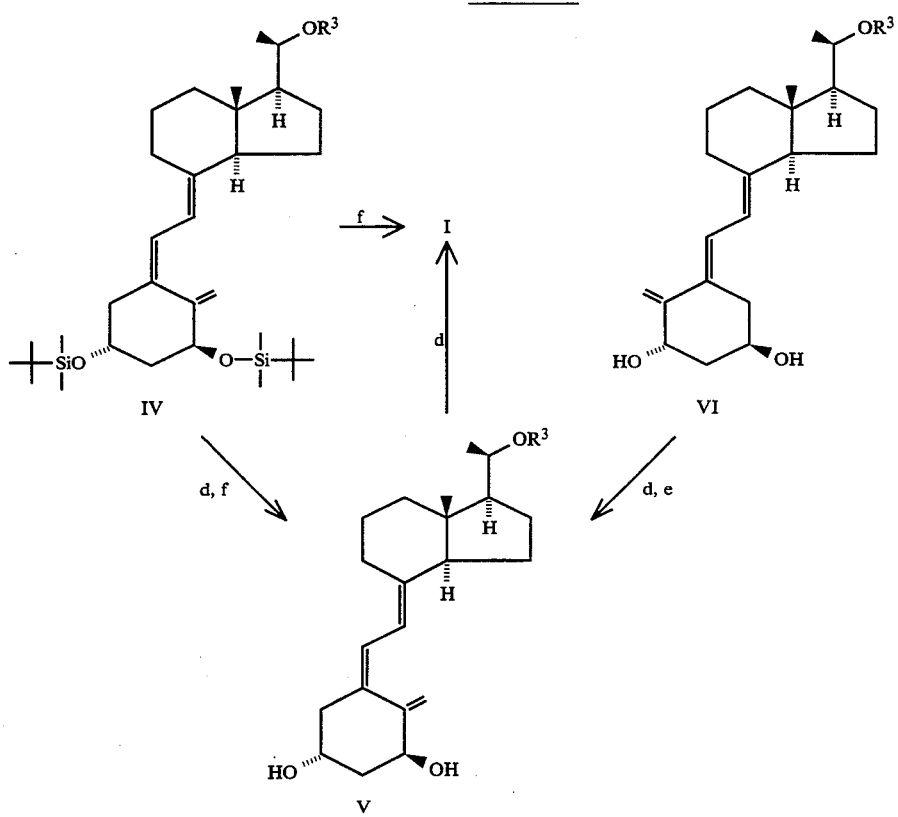

Notes to Scheme 1
a) Oxidation e.g. with $O_2$ with $Cu(AcO)_2$, 2,2'-bipyridyl and 1.4-diazabicyclo[2,2,2]octane as catalyst.
b) Reduction (e.g. with $NaBH_4$).
c) Alkylation with the side chain fragment $R^3$—Z in the presence of base (e.g. KOH, $KOBu^t$ or KH, with or without catalyst (e.g. 18-Crown-6) in solvent; e.g. THF.
d) Optional function group modification in the side chain.
e) Isomerisation with hν - triplet sensitizer, e.g. anthracene.
f) Deprotection with $TBA^+F^-$ or HF.

It should be noted that although the shown intermediates may have hydroxyl groups protected as tert-butyldimethylsilyl ethers, the scope of the invention does not exclude the use of alternative hydroxyl protecting groups well known in the art (such as those described in T. W. Greene, "Protective groups in organic synthesis", Wiley, New York, 1981), together with alternative reactions for deprotection.

The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis, topical or enteral forms are preferred.

In the treatment of respiratory diseases like asthma an aerosol is preferred.

While it is possible for an active ingredient to be administered alone as the raw chemical, it is preferable to present it as a pharmaceutical formulation. Conveniently, the active ingredient comprises from 1 ppm to 0.1% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and intravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid: or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration include liquid or semi-liquid preparations such as liniments, lotions, applicants, oil-in-water or water-in-oil emulsions such as creams, ointments or pastes; or solutions or suspensions such as drops.

For asthma treatment inhalation of powder, self-propelling or spray formulations, dispensed with a spray can, a nebulizer or an atomizer can be used. The formulations, when dispensed, preferably have a particle size in the range of 10 to 100 $\mu$.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$–$C_6$-alkyl hydrocarbons or halogenated $C_1$–$C_6$-alkyl hydrocarbons or mixtures thereof; chlorinated and flourinated $C_1$–$C_6$-alkyl hydrocarbons are especially preferred. Generally, the propellant constitutes 45 to 99.9% w/w of the formulation whilst the active ingredient constitutes 1 ppm to 0.1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including anti-oxidants), emulsifying agents and the like.

The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 0.1–100 $\mu$g, preferably from 0.2–25 $\mu$g, of a compound of formula I are administered. In the topical treatment of dermatological disorders, ointments, creams or lotions containing from 0.1–500 $\mu$g/g, and preferably from 1–100 $\mu$g/g, of a compound of formula I are administered. The oral compositions are formulated, preferably as tablets, capsules, or drops, containing from 0.05–50 $\mu$g, preferably from 0.1–25 $\mu$g, of a compound of formula I, per dosage unit.

The invention will now be further described in the following non-limiting Preparations and Examples:

PREPARATIONS AND EXAMPLES

General

The exemplified compounds I are listed in Table 1. The intermediates of Scheme I referred to in the Preparations are to be identified by numbers with the corresponding formulae in Table 2.

For nuclear magnetic resonance spectra (300 MHz) chemical shift values ($\delta$) are quoted for deuteriochloroform solutions relative to internal tetramethylsilane ($\delta=0$) or chloroform ($\delta=7.25$). The value for a multiplet, either defined (doublet (d), triplet (t), quartet (q)) or not (m) at the approximate mid point is given unless a range is quoted (s=singlet, b=broad). Coupling constants (J) are given in Hertz, and are sometimes approximated to the nearest unit.

Ether is diethyl ether, and was dried over sodium. THF was dried over sodium-benzophenone. Petroleum ether refers to the pentane fraction. Reactions were run at room temperature unless otherwise noted. The work-up procedure referred to involves dilution with the specified solvent (otherwise the organic reaction solvent), extraction with water and then brine, drying over anhydrous $MgSO_4$, and concentration in vacuo to give a residue.

TABLE 1

Exemplified Compounds I (R given in formula II)

| Compound Number | Example Number | Formula (II) | | | |
|---|---|---|---|---|---|
| | | n | $R^1$ | $R^2$ | X |
| 101 | 2 | 1 | H | $Pr^i$ | OH |
| 102 | 3 | 2 | Me | Me | OH |
| 103 | 12 | 2 | —(CH$_2$)$_5$— | | OH |
| 104 | 11 | 3 | H | H | OH |
| 105 | 4 | 3 | Me | Me | OH |
| 106 | 5 | 3 | Et | Et | OH |
| 107 | 9 | 3 | Pr | Pr | OH |
| 108 | 10 | 4 | Me | Me | H |
| 109 | 1 | 4 | Me | Me | OH |
| 110 | 6 | 4 | Et | Et | OH |
| 111 | 7 | 5 | H | H | OH |
| 112 | 8 | 5 | Me | Me | OH |
| 113 | 13 | 6 | Me | Me | OH |

TABLE 2

| Compound Number | Preparation Number | Type (See Scheme 1) | Formula $R^3$ |
|---|---|---|---|
| 4 | 11 | III | —CH$_2$—CH=CMe$_2$ |
| 5 | 33 | III | —(CH$_2$)$_4$—CHMe$_2$ |
| 6 | 9 | III | —CH$_2$—CH[OSi(Me$_2$)Bu$^t$]CHMe$_2$ |
| 7 | 12 | III | —(CH$_2$)$_2$—C(OH)Me$_2$ |
| 8 | 37 | III | —(CH$_2$)$_2$—C(OH)—(CH$_2$)$_4$—CH$_2$ (ring) |
| 9 | 31 | III | —(CH$_2$)$_4$—OSi(Me$_2$)Bu$^t$ |
| 10 | 15 | III | —(CH$_2$)$_3$—C(O-THP)Me$_2$ |
| 11 | 14 | III | —(CH$_2$)$_3$—C(O-THP)Et$_2$ |
| 12 | 26 | III | —(CH$_2$)$_3$—C(OSiMe$_3$)Et$_2$ |
| 13 | 32 | III | —(CH$_2$)$_3$—C(OSiMe$_3$)Pr$^n_2$ |
| 14 | 3 | III | —(CH$_2$)$_4$—C(O-THP)Me$_2$ |
| 15 | 18 | III | —(CH$_2$)$_4$—C(OSiMe$_3$)Me$_2$ |
| 16 | 19 | III | —(CH$_2$)$_4$—C(OSiMe$_3$)Et$_2$ |
| 17 | 22 | III | —(CH$_2$)$_6$—OSi(Me$_2$)Bu$^t$ |
| 18 | 28 | III | —(CH$_2$)$_5$—C(OSiMe$_3$)Me$_2$ |
| 19 | 39 | III | —(CH$_2$)$_6$—C(OSiMe$_3$)Me$_2$ |
| 20 | 35 | IV | —(CH$_2$)$_4$—CHMe$_2$ |
| 21 | 13 | IV | —(CH$_2$)$_2$—C(OH)Me$_2$ |
| 22 | 38 | IV | —(CH$_2$)$_2$—C(OH)—(CH$_2$)$_4$—CH$_2$ (ring) |
| 23 | 36 | IV | —(CH$_2$)$_4$—OSi(Me$_2$)Bu$^t$ |
| 24 | 16 | IV | —(CH$_2$)$_3$—C(O-THP)Me$_2$ |
| 25 | 17 | IV | —(CH$_2$)$_3$—C(O-THP)Et$_2$ |
| 26 | 27 | IV | —(CH$_2$)$_3$—C(OSiMe$_3$)Et$_2$ |
| 27 | 34 | IV | —(CH$_2$)$_3$—C(OSiMe$_3$)Pr$^n_2$ |
| 28 | 25 | IV | —(CH$_2$)$_4$—C(OSiMe$_3$)Me$_2$ |
| 29 | 24 | IV | —(CH$_2$)$_4$—C(OSiMe$_3$)Et$_2$ |
| 30 | 23 | IV | —(CH$_2$)$_6$—OSi(Me$_2$)Bu$^t$ |
| 31 | 29 | IV | —(CH$_2$)$_5$—C(OSiMe$_3$)Me$_2$ |
| 32 | 40 | IV | —(CH$_2$)$_6$—C(OSiMe$_3$)Me$_2$ |
| 33 | 4 | V | —(CH$_2$)$_4$—C(O-THP)Me$_2$ |
| 34 | 10 | VI | —CH$_2$—CH(OH)CHMe$_2$ |

Preparation 1

Compound 2

To a solution of 1(S),3(R)-bis-(tert-butyldimethyl-silyloxy)-20(S)-formyl-9,10-secopregna-5(E), (7E),10(19)-triene (3.44 g, 6 mmol) (1) in N,N-dimethylformamide (150 ml), 1,4-diazabicyclo[2.2.2]octane (600 mg, 5.3 mmol), cupric acetate, monohydrate (90 mg, 0.45 mmol) and 2,2'-bipyridyl (72 mg, 0.45 mmol) were added. Air was bubbled through the well stirred solution for 6 days at 40° C.

The reaction mixture was diluted with ethyl acetate (500 ml), extracted with water (2×100 ml) and saturated aqueous sodium chloride (3×50 ml) and dried over MgSO$_4$. Ethyl acetate was evaporated off, and the solid residue was purified by chromatography (silica gel, 10% ether in petroleum ether as eluant) to give the title compound.

NMR: δ=0.037 (s, 3H), 0.043 (s, 3H), 0.056 (s, 6H), 0.49 (s, 3H), 0.84 (s, 9H), 0.89 (s, 9H), 1.5–2.30 (m, 13H), 2.13 (s, 3H), 2.55 (dd, 1H), 2.70 (t, 1H), 2.89 (bd, 1H), 4.21 (m, 1H), 4.52 (m, 1H), 4.94 (m, 1H), 4.98 (m, 1H), 5.83 (d, 1H), 6.43 (d, 1H) ppm.

Preparation 2

Compound 3 and its 20S-isomer

Compound 2 (Prep. 1) (3.10 g, 5.5 mmol) was dissolved in tetrahydrofuran (140 ml) and sodium borohydride (0.35 g, 3.3 mmol) was added. Methanol was then added dropwise over 15 minutes. The reaction blend was stirred for 20 minutes, then diluted with ethyl acetate (560 ml). The solution was extracted with water (5×150 ml) and saturated aqueous sodium chloride (150 ml), dried over MgSO$_4$ and evaporated to give a colourless oil. The oily residue was purified by chromatography (silica gel, 15% ethyl acetate in petroleum ether as eluant) and crystallization from methanol to give 3.

NMR: δ=0.05 (m, 12H), 0.62 (s, 3H), 0.86 (s, 9H), 0.89 (s, 9H), 1.10–2.10 (m, 14H), 1.15 (d, 3H), 2.30 (bd, 1H), 2.53 (dd, 1H), 2.89 (m, 1H), 2.89 (m, 1H), 3.71 (m, 1H), 4.21 (m, 1H), 4.52 (m, 1H), 4.93 (m, 1H), 4.98 (m, 1H), 5.81 (d, 1H), 6.45 (d, 1H) ppm.

The fractions containing the more polar 20S-isomer were evaporated to give a colourless residue which was crystallized from methanol:

NMR, δ=0.052 (bd, 12H), 0.54 (s, 3H), 0.85 (s, 9H), 0.89 (s, 9H), 1.22 (d, 3H), 1.20–2.10 (m, 14H), 2.30 (bd, 1H), 2.55 (dd, 1H), 2.87 (m, 1H), 3.72 (m, 1H), 4.21 (m, 1H), 4.52 (m, 1H), 4.94 (bs, 1H), 4.98 (m, 1H), 5.82 (d, 1H), 6.44 (d, 1H) ppm.

Preparation 3

Compound 14 ($R^3$=5-(tetrahydro-4-H-pyran-2-yloxy)-5-methyl-1-hexyl)

To a solution of compound 3 (561 mg, 1 mmol) in dry tetrahydrofuran (10 ml) were added potassium hydroxide (0.70 g, 10 mmol), 18-Crown-6 (40 mg) and 2-(6-bromo-2-methyl-2-hexyloxy)-tetrahydro-4H-pyran (Preparation 5a) (2.7 g, 10 mmol) were added. The mixture was stirred vigorously over the week-end, the reaction mixture was filtered, and the filtrate was evaporated in vacuo.

The residue was purified by chromatography (silica gel, 10% ether in petroleum ether as eluant) to give 14 as a colourless oil.

NMR, δ=0.054 (m, 12H), 0.54 (s, 3H), 0.86 (s, 9H), 0.88 (s, 9H), 1.07 (d, J=6, 3H), 1.17 (s, 3H), 1.19 (s, 3H), 1.15–1.95 (m, 23H), 2.02 (t, 1H), 2.20 (bd, 1H), 2.30 (bd, 1H), 2.53 (dd, 1H), 2.85 (m, 1H), 3.10–3.30 (m, 2H), 3.40 (m, 1H), 3.55 (m, 1H), 3.93 (m, 1H), 4.20 (m, 1H), 4.51 (m, 1H), 4.69 (m, 1H), 4.93 (m, 1H), 4.98 (m, 1H), 5.79 (d, J=11, 1H), 6.45 (d, J=H, 1H) ppm.

Preparation 4

1(S),3(R)-Dihydroxy-20(R)-[5'(tetrahydro-4H-pyran-2''-yloxy)-5'-methyl-1'-hexyloxy]-9,10-seco-pregna-5(Z), 7(E),10(19)-triene (Compound 33)

A solution of compound 14 (400 mg, 0.5 mmol) anthracene (200 mg, 1.1 mmol) and triethylamine (1 drop)

in dichloromethane (15 ml) under nitrogen in a Pyrex flask was irradiated with light from a high pressure ultra-violet lamp, type TQ 150Z2 (Hanau), at room temperature for 30 minutes. The solution was filtered and concentrated in vacuo to give the crude intermediate (Compund IV, Scheme 1, $R^3$=5-(tetrahydro-4-H-pyran-2-yloxy)-5-methyl-1-hexyl). This was dissolved in tetrahydrofuran (THF) (15 ml) and tetra-n-butylammonium fluoride trihydrate (1.05 g, 3.3 mmol) was added. The solution was heated at 60° C. under an atmosphere of nitrogen for 1 hour. After cooling, the reaction mixture was partitioned between ethyl acetate (50 ml) and saturated aqueous sodium hydrogen carbonate (10 ml). The organic layer was washed with water (10 ml), dried and concentrated. The residue was purified by chromatography (100 g, silica gel, 50% ethyl acetate in petroleum ether as eluant) to give the desired compound.

NMR, $\delta$=0.56 (s, 3H), 1.07 (d, 3H), 1.18 (s, 3H), 1.20 (s, 3H), 1.1–2.05 (m, 24H), 2.17 (bd, 1H), 2.30 (dd, 1H), 2.57 (dd, 1H), 2.81 (m, 1H), 3.10–3.30 (m, 2H), 3.42 (m, 1H), 3.56 (m, 1H), 3.93 (m, 1H), 4.22 (m, 3H), 4.41 (m, 1H), 4.70 (m, 1H), 5.00 (bs, 1H), 5.33 (bs, 1H), 5.99 (d, 1H), 6.39 (d, 1H) ppm.

Preparation 5a 2-(6-Bromo-2-methyl-2-hexyloxy)-tetrahydro-4H-pyran

To a stirred, ice-cooled solution of ethyl 5-bromopentanoate (18.7 ml) in dried ether (100 ml) was added dropwise over 1 hour a filtered solution of Grignard reagent, prepared from magnesium (10 g) and methyl iodide 25 ml) in dried ether (200 ml). After a further 30 minutes on the ice-bath, the reaction mixture was allowed to warm to room temperature over 30 minutes before being poured onto a stirred, ice-cooled solution of ammonium chloride (30 g) in water (200 ml). After the vigorous reaction had subsided, the ether layer was separated, and the aqueous layer was extracted with more ether. The combined ether layers were washed consecutively with water and saturated aqueous sodium chloride, dried, and concentrated in vacuo to give the crude intermediate (6-bromo-2-methyl-2-hexanol) as a pale yellow oil. This was dissolved in dichloromethane (100 ml), then 3,4-dihydro-2H-pyran (8.9 ml) and pyridinium p-toluenesulfonate (0.8 g) were added at room temperature. After 1 hour, the reaction solution was diluted with ether (250 ml) and extracted consecutively with saturated aqueous sodium hydrogen carbonate (150 ml), water (100 ml) and saturated aqueous sodium chloride (100 ml). After drying and removal of the solvent in vacuo, the product was purified by chromatography (150 g silica gel, 10% ether in petroleum ether as eluant) to give the desired compound as a colourless oil.

NMR: $\delta$=1.20 (s, 3H), 1.22 (s, 3H), 1.40–1.95 (m, 12H), 3.42 (t, 2H), 3.94 (m, 1H), 3.45 (m, 1H), 4.72 (m, 1H) ppm.

Preparation 5b 2-(6-Bromo-3-ethyl-2-hexyloxy)-tetrahydro-4H-pyran

Using a procedure analogous to that of Preparation 5a, the title compound was prepared form ethyl 4-bromobutanoate, and the Grignard reagent derived from ethyl iodide.

NMR in agreement with structure.

Preparation 6

5-Hydroxy-2,2,6-trimethyl-3(E)-heptene

To a solution of diethyl isobutyrylmethylphosphonate (22 g), tetrabutylammonium bromide (4 g) and pivaldehyde (13 ml) in dichloromethane (340 ml) was added 4N aqueous sodium hydroxide solution (140 ml). The mixture was stirred overnight, and, after dilution with water, the organic phase was worked up. The intermediate 5-oxo-2,2,6-trimethyl-3(E)-heptane was then isolated by distillation (b.p. 45°–48° C./0.1 mBar). A stirred, ice-cooled solution of this (5 g) in a 0.4M solution cerium III chloride in methanol (90 ml) was treated portionwise with sodium borohydride (1.4 g). After 10 minutes, the mixture was worked-up (ethyl acetate) to give the title compound as an oil.

NMR: $\delta$=0.87 (d, 3H, J=6.8), 1.02 (s, 9H), 1.50 (bs, 1H), 1.70 (m, 1H), 3.77 (bt, 1H), 5.36 (dd, 1H, J=7.4 and 15.7), 5.65 (dd, 1H, J=15.7 and 0.8). NOTE: This racemic compound was resolved using Sharpless' kinetic resolution procedure (J. Amer. Chem. Soc. 1981, 103, 6237) to give either the S-form (using (−)-di-isopropyl tartrate) or the R-form (using (+)-di-isopropyl tartrate). These resolved forms can be used as starting material for the following steps in the sequence here described for the conversion of the racemate to the side chain building block and then the target compound of Example 2.

Preparation 7

3-Methyl-2-(tert-butyldimethylsilyloxy)-butanal

A solution of 5-hydroxy-2,2,6-trimethyl-3(E)-heptene (Preparation 6) (4.5 g), imidazole (5 g) and tert-butyldimethylsilyl chloride (5 g) in dimethylformamide (50 ml) was stirred for 1 hour. Work-up (ether) and distillation gave the intermediate 5-(tert-butydimethylsilyloxy)-2,2,6-trimethyl-3(E)-heptene as an oil. (b.p. 65°–69° C./0.03 mBar). A solution of this (7 g) in methanol (100 ml) and dichloromethane (320 ml) at −70° C. was treated with ozonised oxygen until the reaction was judged to be complete (tlc analysis) (40 minutes), whereupon triphenylphosphine (9 g) was added and the reaction mixture allowed to warm to room temperature. Work-up (dichloromethane) and distillation gave the title compound as an oil, b.p. 45°–48° C./1 mBar.

NMR $\delta$=0.04 (s, 6H), 0.90 (d, 3H), 0.92 (s, 9H), 0.95 (d, 3H), 2.01 (m, 1H), 3.70 (dd, 1H, J=4.8 and 2.1), 9.58 (d, 1H, J=2.1).

Preparation 8

3-Methyl-2-(tert-butyldimethylsilyloxy)-1-(trifluoromethanesulfonyloxy)butane

A stirred, ice-cooled solution of 3-methyl-2-(tert-butyldimethylsilyloxy)butanal (Preparation 7) (0.5 g) in THF (4 ml) and ethanol (8 ml) was treated with sodium borohydride (0.1 g). After 20 minutes, the reaction mixture was worked-up (ethyl acetate) to give the intermediate 3-methyl-2-(tert-butyldimethylsilyloxy)-1-butanol as an oil. This was dissolved in dichloromethane (5 ml), cooled to 0° C., and treated with pyridine (0.5 ml) and trifluoromethansulphonic anhydride (0.5 ml). After stirring for 1 hour, the reaction mixture was worked-up (ether) to give the title compound as an oil.

NMR: $\delta$=0.07 (s, 3H), 0.08 (s, 3H), 0.90 (s, 9H), 0.90 (d, 3H), 0.93 (d, 3H), 1.84 (m, 1H), 3.75 (m, 1H), 4.34 (dd, 1H, J=9.9 and 6.8), 4.43 (d, 1H, J=9,9 and 3.8).

Preparation 9

1(S),3(R)-Bis(tert-butyldimethylsilyloxy)-20(R)-(3′-methyl-2′-tert-butyldimethylsilyloxy-1′-butoxy)-9,10-secopregna-5(E),7(E),10(19)-triene (Compound 6)

A stirred solution of Compound 3 (0.24 g), 18-Crown-6 (40 mg) and potassium tert-butoxide (0.15 g) in dry THF (4 ml) was treated with 3-methyl-2-tert-butyldimethylsilyloxy-1-trifluoromethanesulphonyloxy)butane (Preparation 8) (0.3 g). After 15 minutes, the reaction mixture was worked-up (ether), and the residue purified by chromatography (silica gel, 2% ether in petroleum ether as eluant to give the title compound as an approx. equal mixture of diastereoisomers (epimers as position 2′).

NMR $\delta = 0.0$–0.12 (m, 18H), 0.53 and 0.54 (2s, 3H), 0.60–2.65 (m, 52H), 2.87 (m, 1H), 3.17 (m, 1H), 3.23 (m, 1H), 3.44 (m, 1H), 3.55 (m, 1H), 4.21 (m, 1H), 4.53 (m, 1H), 4.93 (m, 1H), 4.98 (m, 1H), 5.80 (d, 1H, J=11.4), 6.46 (d, 1H, J=11.4).

Preparation 10

1(S),3(R)-Dihydroxy-20(R)-(2′-hydroxy-3′-methyl-1′-butoxy)-9,10-secopregna-5(E),7(E),10(19)-triene (Compound 34)

A stirred solution of 1(S),3(R)-bis(tert-butyldimethylsilyloxy)-20(R)-(3′-methyl-2′-tert-butyldimethylsilyloxy-1′-butoxy)-9,10-secopregna-5(E), 7(E),10(19)-triene (Compound 6) (0.2 g) and tetrabutylammonium fluoride (0.7 g) in THF (5 ml) was heated at 60° C. under nitrogen for 1 hour. After cooling, the reaction mixture was worked-up (ethyl acetate). Purification by chromatography (silica gel; ethyl acetate as eluant) gave the title compound.

NMR: $\delta = 0.58$ and 0.60 (2s, 3H), 0.92 (d, 3H, J=6.9), 0.98 (d, 3H, J=6.9), 1.05–2.70 (m, 20H), 2.86 (m, 2H), 3.13–3.63 (m, 5H), 4.22 (m, 1H), 4.48 (m, 1H), 4.97 (m, 1H), 5.12 (m, 1H), 5.87 (d, 1H, J=11.4), 6.57 (d, 1H, J=11.4).

Preparation 11

1(S),3(R)-Bis-[tert-butyl(dimethylsilyl)oxy]-20(R)-(3-methylbut-2-en-1-yloxy)-9,10-secopregna-5(E),-7(E),10(19)-triene (Compound 4)

To a solution of compound 3 (0.61 g) in dry THF (10 ml) were added powdered potassium hydroxide (1.2 g), 18-Crown-6 (80 mg) and 3,3-dimethylallyl bromide (2.2 g). After stirring at room temperature for 24 hours, the mixture was partitioned between ether and water. The ether layer was washed with brine, dried and concentrated in vacuo to give an oil. Purification by chromatography (silica gel; 2% to 5% ether in petroleum ether as eluent) followed by crystallization from methanol gave 4 as needles.

NMR: $\delta = 0.05$ (bs, 12H), 0.55 (s, 3H), 0.86 (s, 9H), 0.89 (s, 9H), 1.10 (d, 3H), 1.65 (m, 3H), 1.72 (m, 3H), 1.05–1.82 (m, 10H), 1.90 (m, 1H), 2.03 (bt, 1H), 2.14 (m, 1H), 2.30 (m, 1H), 2.54 (dd, 1H), 2.87 (m, 1H), 3.30 (m, 1H), 3.78 (m, 1H), 4.06 (m, 1H), 4.21 (m, 1H), 4.52 (m, 1H), 4.93 (m, 1H), 4.98 (m, 1H), 5.33 (m, 1H), 5.80 (d, 1H, J=11.5), 6.46 (d, 1H, J=11.5).

Preparation 12

1(S),3(R)-Bis-[tert-butyl(dimethylsilyl)oxy]-20(R)-(3-hydroxy-3-methyl-1-butoxy-9,10-secopregna-5(E),-7(E),10(19)-triene (Compound 7)

NB: This preparation illustrates the protection of the triene system of III as an $SO_2$-adduct to allow efficient functional group modification in the side chain.

A solution of compound 4 (100 mg) in a few drops of ether was treated at $-10°$ C. with liquid sulphur dioxide (3 ml). The stirred mixture was allowed to warm spontaneously under a slow stream of nitrogen, and after 30 minutes the residual volatile material was removed on the rotary evaporator. The residue was dissolved in THF (2 ml) and treated with a mixture prepared by adding THF (1 ml) to a solution of mercury II acetate (100 mg) in water (1 ml). The reaction mixture was stirred at 5° C. for 18 hours and then treated with 3N NaOH (3 ml) followed by a solution of $NaBH_4$ (0.05 g) in 3N NaOH (2 ml). Ethyl acetate was added and the mixture filtered through celite. The organic layer was washed with brine, dried and concentrated in vacuo to give a gum. This was dissolved/suspended in 96% ethanol (4 ml) together with sodium bicarbonate (0.2 g) and the stirred mixture was heated under reflux under nitrogen for 80 minutes. After cooling, the ethyl acetate was added and the mixture was extracted with water. The organic layer was washed with water. The organic layer was washed with brine, dried and concentrated in vacuo to give a residue. Purification by chromatography (silica gel, 5% to 30% ether in petroleum ether as eluent) gave 7.

NMR: $\delta = 0.05$ (m, 12H), 0.54 (s, 3H), 0.85 (s, 9H), 0.89 (s, 9H), 1.13 (d, 3H), 1.22 (s, 3H), 1.23 (s, 3H), 1.00–2.20 (m, 15H), 2.30 (bd, 1H), 2.53 (dd, 1H), 2.86 (m, 1H), 3.27 (m, 1H), 3.45 (m, 1H), 3.55 (s, 1H), 3.83 (m, 1H), 4.21 (m, 1H), 4.52 (m, 1H), 4.93 (m, 1H), 4.98 (m, 1H), 5.79 (d, 1H, J=11.4), 6.45 (d, 1H, J=11.4).

Preparation 13

1(S),3(R)-Bis-[tert-butyl(dimethylsilyl)oxy]-20(R)-(3-hydroxy-3-methyl-1-butoxy-9,10-secopregna-5(Z),7(E),10(19)-triene (Compound 21)

A solution under nitrogen of compound 7 (40 mg) in dichloromethane (4 ml) containing anthracene (20 mg) and triethylamine (50 μl) in a Pyrex flask was irradiated with light from a high pressure ultra-violet lamp (type TQ150Z2 (Hanau) at 15° C. for 30 minutes. The reaction mixture was filtered and concentrated in vacuo to give a residue. Purification by chromatography (silica gel, 30% ether in petroleum ether as eluent) gave 21.

NMR in agreement with structure.

Preparation 14

Compound 11 ($R^3$=4-(tetrahydro-4H-pyran-2-yloxy)-4-ethyl-1-hexyl)

To a solution of compound 3 (561 mg, 1.0 mmol) in dry tetrahydrofuran (10 ml) potassium tert-butoxide (0.4 g, 3.6 mmol), 18-Crown-6 (80 mg) and 2-(6-bromo-3-ethyl-3-hexyloxy-tetrahydro-4H-pyran (Preparation 5b) (1.08 g, 3.68 mmol) were added. The mixture was stirred overnight and diluted with ethyl acetate (60 ml), then washed with water (3 × 10 ml) and saturated aqueous sodium chloride (10 ml), dried over $MgSO_4$ and concentrated in vacuo. The compound was then purified by chromatography (150 g silica gel, 10% ether in petroleum ether as eluant) to give the desired compound as a colourless oil.

NMR: $\delta = 0.05$ (m, 12H), 0.55 (s, 3H), 0.82 (m, 6H), 0.86 (s, 9H), 0.89 (s, 9H), 1.07 (d, 3H), J=6), 1.0–2.1 (m, 25H), 2.03 (bt, 1H), 2.18 (bd, 1H), 2.30 (bd, 1H), 2.54 (dd, 1H), 2.87 (bd, 1H), 3.12 (m, 1H), 3.25 (m, 1H), 3.42 (m, 1H), 3.55 (m, 1H), 3.95 (m, 1H), 4.21 (m, 1H), 4.52

(m, 1H), 4.68 (m, 1H), 4.92 (bs, 1H), 4.98 (bs, 1H), 5.79 (d, 1H, J=11), 6.46 (d, 1H, J=11) ppm.

Preparation 15

Compound 10 (R$^3$=4-(tetrahydro-4H-pyran-2-yloxy)-4-ethyl-1-pentyl)

By following the procedure of Preparation 14 and substituting 2-(5-bromo-2-methyl-2-pentyloxy)-tetrahydro-4H-pyran for 2-(6-bromo-3-ethyl-3-hexyloxy)-tetrahydro-4H-pyran, the desired compound was obtained as a colourless oil.

NMR: δ=0.05 (m, 12H), 0.55 (s, 3H), 0.86 (s, 9H), 0.89 (s, 9H), 1.07 (d, 3H, J=6), 1.19 (s, 3H), 1.20 (s, 3H), 0.9–2.0 (m, 21H), 2.03 (m, 1H), 2.16 (bd, 1H), 2.30 (bd, 1H), 2.55 (dd, 1H), 2.87 (bd, 1H), 3.15 (m, 1H), 3.25 (m, 1H), 3.43 (m, 1H), 3.55 (m, 1H), 3.93 (m, 1H), 4.21 (m, 1H), 4.52 (m, 1H), 4.71 (m, 1H), 4.93 (bs, 1H), 4.98 (bs, 1H), 5.80 (d, 1H, J=11), 6.46 (d, 1H, J=11) ppm.

Preparation 16

Compound 24 (R$^3$=4-(tetrahydro-4H-pyran-2-yloxy)-4-methyl-1-pentyl)

A solution of the compound 10 prepared in Preparation 15 (200 mg, 0.27 mmol), anthracene (200 mg, 1.1 mmol) and triethylamine (1 drop) in dichloromethane (15 ml) under nitrogen in a Pyrex flask was irradiated with light from a high pressure ultraviolet lamp, type TQ150Z2 (Hanau) at about 10° C. for 30 minutes. The reaction blend was filtered, concentrated in vacuo and purified by chromatography (30 g silica gel, 50% ether in petroleum ether as eluant) to give the desired compound as a colourless oil.

NMR: δ=0.05 (m, 12H), 0.53 (s, 3H), 0.87 (m, 18H), 1.06 (d, 3H, J=6), 1.18 (s, 3H), 1.20 (s, 3H), 1.0–1.9 (m, 21H), 1.98 (bt, 1H), 2.16 (m, 2H), 2.43 (dd, 1H), 2.82 (bd, 1H), 3.18 (m, 1H), 3.24 (m, 1H), 3.43 (m, 1H), 3.53 (m, 1H), 3.93 (m, 1H), 4.18 (m, 1H), 4.36 (m, 1H), 4.70 (m, 1H), 4.85 (bs, 1H), 5.16 (bs, 1H), 5.99 (d, 1H, J=11), 6.24 (d, 1H, J=11) ppm.

Preparation 17

Compound 25 (R$^3$=4-(tetrahydro-4H-pyran-2-yloxy)-4-ethyl-1-hexyl)

By following the procedure of Preparation 16 and substituting the compound 11 prepared in Preparation 14 for the compound 10 prepared in Preparation 15, the desired compound was obtained as a colourless oil.

NMR: δ=0.05 (m, 12H), 0.53 (s, 3H), 0.82 (m, 6H), 0.87 (s, 18H), 1.06 (d, 3H, J=6), 1.0–1.9 (m, 25H), 1.98 (bt, 1H), 2.19 (m, 2H), 2.44 (dd, 1H), 2.82 (bd, 1H), 3.12 (m, 1H), 3.25 (m, 1H), 3.43 (m, 1H), 3.55 (m, 1H), 3.93 (m, 1H), 4.18 (m, 1H), 4.36 (m, 1H), 4.69 (m, 1H), 4.85 (bs, 1H), 5.16 (bs, 1H), 5.99 (d, 1H, J=11), 6.24 (d, 1H, J=11) ppm.

Preparation 18

Compound 15 (R$^3$=5-trimethylsilyloxy-5-methyl-1-hexyl)

To a solution of 3 (561 mg, 1.0 mmol) in dry tetrahydrofuran (10 ml) potassium tert-butoxide (0.65 g, 5.8 mmol), 18-Crown-6 (120 mg) and 6-bromo-2-methyl-2-trimethylsilyloxy-hexan (1.4 ml, 5.0 mmol) were added. The reaction mixture was stirred for 2 hours and worked-up (ether). The crude product was purified by chromatography (40 g silica gel, 2% ether in petroleum ether as eluant) to give a colourless oil, which crystallized from methanol.

M.p.: 75.5°–77.5° C.

NMR: δ=0.05–0.09 (m, 21H), 0.55 (s, 3H), 0.86 (s,9H), 0.89 (s, 9H), 1.07 (d, 3H), 1.18 (s, 6H), 1.15–2.0 (m, 17H), 2.02 (t, 1H), 2.17 (d, 1H), 2.31 (d, 1H), 2.55 (dd, 1H), 2.85 (bd, 1H), 3.15 (m, 1H), 3.26 (m, 1H), 3.56 (m, 1H), 4.21 (m, 1H). 4.53 (m, 1H), 4.93 (bs, 1H), 4.99 (bs, 1H), 5.79 (d, 1H), 6.46 (d, 1H) ppm.

Preparation 19

Compound 16 (R$^3$=5-trimethylsilyloxy-5-ethyl-1-heptyl)

To a solution of compound 3 (561 mg, 1.0 mmol) in dry tetrahydrofuran (10 ml), potassium tert-butoxide 0.45 g, 4.0 mmol), 18-Crown-6 (80 mg) and 7-bromo-3-ethyl-3-trimethylsilyloxy-heptane (0.44 ml, 1.5 mol) were added. The reaction blend was stirred for 4 hours and worked-up (ethyl acetate). The crude product was purified by chromatography (100 g silica gel, 5% ether in petroleum ether as eluant) to give a colourless oil which crystallized from methanol.

M.p.: 70.5°–72.5° C.

NMR: δ=0.04–0.10 (m, 21H), 0.55 (s, 3H), 0.80 (dt, 6H), 0.86 (s, 9H), 0.89 (s, 9H), 1.07 (d, 3H), 1.43 (dq, 4H), 1.00–1.96 (m, 17H), 2.04 (bt, 1H), 2.17 (bd, 1H), 2.30 (bd, 1H), 2.55 (dd, 1H), 2.86 (bd, 1H), 3.15 (m, 1H), 3.26 (m, 1H), 3.58 (m, 1H), 4.21 (m, 1H), 4.52 (m, 1H), 4.93 (m, 1H), 4.98 (m, 1H), 5.80 (d, 1H, J=11.3), 6.46 (d, 1H, J=11.3) ppm.

Preparation 20

1-(tert-butyl-dimethylsilyloxy)-6-chloro-hexane

To a solution of 6-chloro-hexan-1-ol (6.8 ml, 75.4 mmol) in dry dichloromethane (100 ml) tert-butyldimethylsilylchloride (12.5 g, 83 mmol) and imidazol (10.21 g, 150 mmol) were added, and the reaction mixture stirred overnight at room temperature. Work-up (dichloromethane) and distillilation gave the title compound as an oil.

B.p.: 130°–134° C./12 mBar.

NMR: δ=0.03 (s, 6H), 0.88 (s, 9H), 1.27–1.60 (m, 6H), 1.77 (m, 2H), 3.52 (t, 2H), 3.59 (t, 2H) ppm.

Preparation 21

1-(tert-butyldimethylsilyloxy)-6-iodo-hexane

A solution of sodium iodide (13.5 g, 90 mmol) and 1-(tert-butyldimethylsilyloxy)-6-chloro-hexane (Preparation 20) (8.35 g, 22 mmol) in acetone (70 ml) was refluxed overnight. The reaction mixture was cooled to room temperature and filtered. The filtrate was worked-up (hexane) to give the desired compound as yellow oil.

NMR: δ=0.03 (s, 6H), 0.88 (s, 9H), 1.22–1.60 (m, 6H), 1.82 (m, 2H), 3.18 (t, 2H), 3.59 (t, 2H) ppm.

Preparation 22

Compound 17 (R$^3$=6-(tert-butyldimethylsilyloxy)-1-hexyl)

To a solution of compound 3 (516 mg, 0.9 mmol) in dry tetrahydrofuran (8 ml), potassium tert-butoxide (0.65 g, 5.8 mmol), 18-Crown-6 (100 mg) and 1-tert-butyldimethylsilyloxy)-6-iodo-hexane (Preparation 21) (1.70 ml, 5 mmol) were added. The mixture was stirred overnight and worked-up (ether). The crude product was purified by chromatography (100 g silica gel, 30% toluene in petroleum ether as eluant) to give a colourless oil which crystallized from methanol.

M.p.: 84°–87° C.

NMR: δ=0.03 (s, 6H), 0.06 (m, 12H), 0.54 (s, 3H), 0.86 (s, 9H), 0.87 (s, 9H), 0.89 (s, 9H), 1.07 (d, 3H), 1.10–1.82 (m, 18H), 1.92 (m, 1H), 2.03 (bt, 1H), 2.14 (bd, 1H), 2.30 (bd, 1H), 2.52 (dd, 1H), 2.87 (m, 1H), 3.22 (m, 2H), 3.55 (m, 1H), 3.58 (t, 2H), 4.21 (m, 1H), 4.52 (m, 1H), 4.93 (m, 1H), 4.98 (m, 1H), 5.80 (d, 1H, J=11.4), 6.46 (d, 1H, J=11.4) ppm.

Preparation 23

Compound 30 ($R^3$=6-(tert-butyldimethylsilyloxy)-1-hexyl)

A solution of the compound 17 prepared in Preparation 22 (238 mg, 0.3 mmol), anthracene (150 mg, 0.8 mmol) and triethylamine (2 drops) in dichloromethane (12 ml) under nitrogen in a Pyrex flask was irradiated with light from a high pressure ultra-violet lamp, type TQ150Z2 (Hanau) at 15° C. for 30 minutes. The reaction mixture was filtered, concentrated in vacuo and purified by chromatography (40 g silica gel, 10% ether in petroleum ether as eluant) to give the desired compound as a colourless oil.

NMR: $\delta$=0.03 (s, 6H), 0.04 (m, 6H), 0.05 (s, 6H), 0.53 (s, 3H), 0.86 (s, 9H), 0.87 (s, 9H), 0.88 (s, 9H), 1.06 (d, 3H), 1.00–2.30 (m, 22H), 2.44 (dd, 1H), 2.82 (bd, 1H), 3.20 (m, 2H), 3.55 (m, 1H), 3.58 (t, 2H), 4.18 (m, 1H), 4.36 (m, 1H), 4.86 (m, 1H), 5.16 (m, 1H), 5.99 (d, 1H, J=11.3), 6.24 (d, 1H, J=11.3) ppm.

Preparation 24

Compound 29 ($R^3$=5-trimethylsilyloxy)-5-ethyl-1-heptyl)

A solution of the compound 16 prepared in Preparation 19 (300 mg, 0.4 mmol), anthracene (300 mg, 1.7 mmol) and triethylamine (1 drop) in dichloromethane (15 ml) under nitrogen in a Pyrex flask was irradiated with light from a high pressure ultra-violet lamp, type TQ150Z2 (Hanau) at 15° C. for 45 minutes. The reaction mixture was filtered, concentrated in vacuo and purified by chromatography (15 g silica gel, 30% toluene in petroleum ether as eluant) to give the desired compound as a colourless oil.

NMR: $\delta$=0.05 (s, 6H), 0.06 (s, 6H), 0.08 (s, 9H), 0.54 (s, 3H), 0.80 (ds, 6H), 0.87 (s, 18H), 1.07 (d, 3H), 1.43 (bq, 4H), 1.00–2.25 (m, 20H), 2.45 (dd, 1H), 2.82 (bd, 1H), 3.15 (m, 1H), 3.24 (m, 1H), 3.57 (m, 1H), 4.18 (m, 1H), 4.35 (m, 1H), 4.86 (m, 1H), 5.16 (m, 1H), 5.99 (d, 1H, J=11.3), 6.24 (d, 1H, J=11.3) ppm.

Preparation 25

Compound 28 ($R^3$=5-trimethylsilyloxy-5-methyl-1-hexyl)

A solution of the compound 15 prepared in Preparation 18 (3.50 g, 4.7 mol), anthracene (2.2 g, 12 mmol) and triethylamine (0.5 ml) in dichloromethane (175 ml) under nitrogen in a Pyrex flask was irradiated with light from a high pressure ultra-violet lamp, type TQ150Z2 (Hanau) at 15° C. for 2 hours. The reaction mixture was filtered, concentrated in vacuo and purified by chromatography (75 g silica gel, 5% ether in petroleum ether as eluant) to give the desired compound as a colourless oil.

NMR: $\delta$=0.05–0.10 (m, 21H), 0.54 (s, 3H), 0.87 (s, 18H), 1.06 (d, 3H), 1.18 (s, 6H), 1.15–1.90 (m, 17H), 1.99 (t, 1H), 2.15 (m, 1H), 2.17 (m, 1H), 2.44 (dd, 1H), 2.81 (m, 1H), 3.20 (m, 2H), 3.56 (m, 1H), 4.18 (m, 1H), 4.36 (m, 1H), 4.86 (bd, 1H), 5.16 (bs, 1H), 5.98 (d, 1H), 6.23 (d, 1H) ppm.

Preparation 26

Compound 12 ($R^3$=4-trimethylsilyloxy-4-ethyl-1-hexyl)

A solution of potassium tert-butoxide (1.95 g, 17 mmol) in dry tetrahydrofuran (15 ml) was added dropwise via a syringe over 40 minutes to a solution of compound 3 (1.68 g, 3 mmol), 18-Crown-6 (600 mg) and 6-bromo-3-ethyl-3-trimethylsilyloxy-hexane (2.53 ml, 9 mmol) in dry tetrahydrofuran (20 ml) stirred under nitrogen. The resulting solution was stirred for 45 minutes and worked-up (hexane). The crude product was purified by chromatrography (140 g silica gel, 30% toluene in petroleum ether as eluant) to give a colourless oil which crystallized from methanol.

M.p.: 52°–57° C.

NMR: $\delta$=0.05–0.1 (m, 21H), 0.55 (s, 3H), 0.80 (dt, 6H), 0.86 (s, 9H), 0.89 (s, 9H), 1.07 (d, 3H), 1.10–2.05 (m, 20H), 2.18 (d, 1H), 2.30 (d, 1H), 2.54 (dd, 1H), 2.86 (bd, 1H), 3.12 (m, 1H), 32.5 (m, 1H), 3.55 (m, 1H), 4.21 (m, 1H), 4.52 (m, 1H), 4.93 (bs, 1H), 4.98 (bs, 1H), 5.79 (d, 1H), 6.46 (d, 1H) ppm.

Preparation 27

Compound 26 ($R^3$=4-trimethylsilyloxy)-4-ethyl-1-hexyl)

A solution of the compound 12 prepared in Preparation 26 (1.0 g, 1.3 mmol), anthracene (1.0 g, 5.6 mmol) and triethylamine (3 drops) in dichloromethane (70 ml) under nitrogen in a Pyrex flask was irradiated with light from a high pressure ultra-violet lamp, type TQ150Z2 (Hanau) at 15° C. for 55 minutes. The reaction mixture was filtered, concentrated in vacuo, and purified by chromatography (35 g silica gel, 2% ether in petroleum ether as eluant) to give the desired compound as a colourless oil.

NMR: $\delta$=0.05–0.10 (m, 21H), 0.54 (s, 3H), 0.80 (dt, 6H), 0.87 (s, 18H), 1.06 (d, 3H), 1.0–2.05 (m, 20H), 2.16 (d, 1H), 2.20 (m, 1H), 2.43 (dd, 1H), 2.81 (dd, 1H), 3.12 (m, 1H), 3.24 (m, 1H), 3.55 (m, 1H), 4.18 (m, 1H), 4.35 (m, 1H), 4.85 (bd, 1H), 5.16 (bs, 1H), 5.98 (d, 1H), 6.23 (d, 1H) ppm.

Preparation 28

Compound 18 ($R^3$=6-methyl-6-trimethylsilyloxy-1-heptyl)

A solution of 18-Crown-6 (264 mg, 1 mmol) in dry tetrahydrofuran (4 ml) was added dropwise via a syringe over 3 minutes to a mixture of compound 3 (561 mg, 1 mmol), 7-bromo-2-methyl-2-trimethylsilyloxy-heptane (1.5 ml, 4 mmol) and potassium hydride (0.6 ml, 20% suspension in oil) stirred under nitrogen. The resulting solution was stirred for 3 hours and worked-up (ether). The crude product was purified by chromatography (75 g silica gel, 5% ether in petroleum ether as eluant) to give a colourless oil which crystallized from methanol.

NMR: $\delta$=0.06 (m, 12H), 0.08 (s, 9H), 0.54 (s, 3H), 0.86 (s, 9H), 0.89 (s, 9H), 1.07 (d, 3H), 1.18 (s, 6H), 1.00–1.83 (m, 18H), 1.90 (m, 1H), 2.03 (bt, 1H), 2.15 (bd, 1H), 2.31 (bd, 1H), 2.55 (dd, 1H), 2.87 (bd, 1H), 3.20 (m, 1H), 3.53 (m, 1H), 4.21 (m, 1H), 4.53 (m, 1H), 4.93 (m, 1H), 4.98 (m, 1H), 5.80 (d, 1H, J=11.4), 4.46 (d, 1H, J=11.4) ppm.

Preparation 29

Compound 31 ($R^3$=6-methyl-6-trimethylsilyloxy-1-heptyl)

A solution of the compound 18 prepared in Preparation 28 (400 mg, 0152 mmol), anthracene (300 mg, 1.7 mmol) and triethylamine (3 drops) in dichloromethane (20 ml) under nitrogen in a Pyrex flask was irradiated with light from a high pressure ultra-violet lamp, type TQ150Z2 (Hanau) at 15° C. for 30 minutes. The reaction mixture was filtered, concentrated in vacuo and purified by chromatography (35 g silica gel, 5% ether in petroleum ether as eluant) to give the desired compound as a colourless gum.

NMR: δ=0.05 (m, 12H), 0.08 (s, 9H), 0.53 (s, 3H), 0.87 (s, 18H), 1.06 (d, 3H), 1.18 (s, 6H), 1.00–2.30 (m, 22H), 2.44 (dd, 1H), 2.81 (bd, 1H), 3.21 (m, 2H), 3.54 (m, 1H), 4.18 (m, 1H), 4.37 (m, 1H), 4.86 (m, 1H), 5.17 (m, 1H), 5.99 (d, 1H, J=11.3), 6.24 (d, 1H, J=11.3) ppm.

Preparation 30

1-(tert-butyldimethylsilyloxy)-4-chloro-butane

To a solution of 4-chloro-butan-1-ol (10 ml, 100 mmol) in dry dichlormethane (100 ml) tert-butyldimethylsilylchloride (20.8 g, 120 mmol) and imidazol (13.61 g, 200 mmol) were added, and the reaction mixture was stirred overnight at room temperature. Work-up (ethyl acetate) distillation gave the title compound as an oil.

B.p.: 89°–92° C./12 mBar.

NMR: δ=0.04 (s, 6H9, 0.88 (s, 9H), 1.65 (m, 2H), 1.84 (m, 2H), 3.56 (t, 2H), 3.63 (t, 2H) ppm.

Preparation 31

Compound 9 ($R^3$=4-(tert-butyldimethylsilyloxy)-1-butyl)

A solution of 18-Crown-6 (264 mg, 1 mmol) in dry tetrahydrofuran (4 ml) was added dropwise via a syringe over 2 minutes to a mixture of compound 3 (561 mg, 1 mmol 4-chloro-1-tert-butyldimethylsilyloxy-butane (Preparation 30) (1.5 ml, 5 mmol) and potassium hydride (0.6 ml, 20% suspension in oil) stirred under nitrogen. The resulting solution was stirred for 3½ hours and worked-up (ether). The crude product was purified by chromatography (75 g silica gel, 5% ether in petroleum ether as eluant) to give a colourless gum which crystalized from methanol.

M.p.: 91°–96° C.

NMR: δ=0.03 (m, 6H), 0.06 (s, 12H), 0.54 (s, 3H), 0.86 (s, 9H), 0.88 (s, 9H), 0.89 (s, 9H), 1.06 (d, 3H), 1.00–1.83 (m, 14H), 1.92 (m, 1H), 2.03 (bt, 1H), 2.14 (bd, 1H), 2.30 (bd, 1H), 2.54 (dd, 1H), 2.86 (bd, 1H), 3.23 (m, 2H), 3.57 (dd, 1H), 3.61 (t, 2H), 4.21 (m, 1H), 4.53 (m, 1H), 4.93 (m, 1H), 4.98 (m, 1H), 5.79 (d, 1H, J=11.4), 6.46 (d, 1H), J=11.4) ppm.

Preparation 32

Compound 13 ($R^3$=4-trimethylsilyloxy-4-(1-propyl)-1-heptyl)

The compound was prepared according to the procedure described in Preparation 31, except that the 4-chloro-1-tert-butyldimethoxy-butane was substituted with 7-bromo-4-(1-propyl)-4-trimethylsilyloxy-heptane.

NMR: δ=0.05 (m, 12H), 0.07 (s, 9H), 0.55 (s, 3H), 0.86 (s, 9H), 0.87 (m, 6H), 0.89 (s, 9H), 1.07 (d, 3H), 1.00–1.85 (m, 22H), 1.91 (m, 1H), 2.03 (bt, 1H), 2.19 (bd, 1H), 2.30 (bd, 1H), 2.55 (dd, 1H), 2.87 (bd, 1H), 3.11 (m, 2H), 3.25 (dd, 1H), 3.55 (t, 1H), 4.22 (m, 1H), 4.53 (m, 1H), 4.93 (m, 1H), 4.93 (m, 1H), 4.98 (m, 1H), 5.80 (d, 1H, J=11.3), 6.46 (d, 1H), J=11.3) ppm.

Preparation 33

Compound 5 ($R^3$=5-methyl-1-hexyl)

The compound was prepared according to the procedure described in Preparation 31, except that the 4-chloro-1-tert-butyldimethylsilyloxy-butane was substituted with 1-bromo-5-methyl-hexane.

M.p.: 79.5°–81° C.

NMR: δ=0.06 (m, 12H), 0.55 (s, 3H), 0.85 (s, 6H), 0.86 (s, 9H), 0.89 (s, 9H), 1.07 (d, 3H), 1.00–1.85 (m, 17H), 1.91 (m, 1H), 2.03 (bt, 1H), 2.16 (bd, 1H), 2.31 (bd, 1H), 2.55 (dd, 1H), 2.87 (bd, 1H), 3.16 (m, 2H), 3.24 (m, 1H), 3.55 (m, 1H), 4.21 (m, 1H), 4.53 (m, 1H), 4.93 (m, 1H), 4.98 (m, 1H), 5.80 (d, 1H, J=11.4), 6.46 (d, 1H), J=11.4) ppm.

Preparation 34

Compound 27 ($R^3$=4-trimethylsilyloxy-4-(1-propyl)-1-heptyl)

The compound was prepared according to the procedure described in Preparation 23, except that the compound 17 prepared in Preparation 22 was substituted with the compound 13 prepared in Preparation 32.

NMR: δ=0.04 (m, 6H), 0.05 (s, 6H), 0.07 (s, 9H), 0.54 (s, 3H), 0.80–0.93 (m, 24H), 1.06 (d, 3H), 1.00–2.07 (m, 24H), 2.19 (m, 2H), 2.45 (dd, 1H), 2.82 (bd, 1H), 3.12 (m, 1H), 3.24 (m, 2H), 3.55 (m, 1H), 4.18 (m, 1H), 4.36 (m, 1H), 4.86 (m, H), 5.17 (m, 1H), 5.99 (d, 1H, J=11.2), 6.24 (d, 1H, J=11.2) ppm.

Preparation 35

Compound 20 ($R^3$=5-methyl-1-hexyl)

The compound was prepared according to the procedure described in Preparation 23, except that compound 17 prepared in Preparation 22 was substituted with compound 5 prepared in Preparation 33.

NMR: δ=0.05 (s, 6H), 0.06 (s, 6H), 0.53 (s, 3H), 0.85 (d, 6H), 0.87 (s, 18H), 1.06 (d, 3H), 1.00–1.92 (m, 18H), 1.98 (bt, 1H), 2.18 (m, 2H), 2.44 (dd, 1H), 2.82 (bd, 1H), 3.18 (m, 2H), 3.55 (m, 1H), 4.17 (m, 1H), 4.36 (m, 1H), 4.86 (m, 1H), 5.16 (m, 1H), 5.99 (d, 1H, J=11.3), 6.24 (d, 1H, J=11.3) ppm.

Preparation 36

Compound 23 ($R^3$=4-tert-butyldimethylsilyloxy-1-butyl)

The compound was prepared according to the procedure described in Preparation 23, except that compound 17 prepared in Preparation 22 was substituted with compound 9 prepared in Preparation 31.

NMR: δ=0.05 (m, 18H), 0.53 (s, 3H), 0.87 m, 27H), 1.06 (d, 3H), 1.00–2.30 (m, 18H), 2.44 (dd, 1H), 2.82 (bd, 1H), 3.22 (m, 2H), 3.57 (m, 1H), 3.61 (t, 1H), 4.18 (m, 1H), 4.36 (m, 1H), 4.86 (m, 1H), 5.17 (m, 1H), 5.99 (d, 1H, J=11.3), 6.24 (d, 1H, J=11.3) ppm.

Preparation 37

Compound 8 ($R^3$=2-(1-hydroxycyclohexyl)ethyl)

Using the procedure of Preparation 11, but substituting 2-cyclohexylidene-1-bromoethane (2.5 g) for the 3,3-dimethylallyl bromide the intermediate compound III

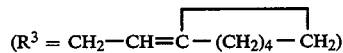

($R^3 = CH_2-CH=C-(CH_2)_4-CH_2$)

was obtained. This compound (100 mg) was substituted for compound 4 in the procedure of Preparation 12 to give 8.

NMR in agreement with structure.

Preparation 38

Compound 22 ($R^3$=2-(1-hydroxycyclohexyl)ethyl)

The compound was prepared using the procedure of Preparation 13, but substituting compound 8 for compound 7.

NMR in agreement with structure.

Preparation 39

Compound 19 ($R^3$ = 7-methyl-7-trimethylsilyloxy-1-octyl)

The compound was prepared using the procedure of Preparation 28, but substituting 8-bromo-2-methyl-2-trimethylsilyloxy-octane for the 7-bromo 2-methyl-2-trimethylsilyloxy-heptane.

NMR in agreement with structure.

The 8-bromo-2-methyl-2-trimethylsilyloxy-octane used in the Preparation was prepared analogously to the method described for lower homologues in our PCT/DK89/00079.

B.p.: 92°–95° C./0.1 mmHg.

NMR: $\delta$ = 0.09 (s, 9H), 1.18 (s, 6H), 1.2–1.5 (m, 8H), 1.85 (m, 2H), and 3.40 (t, 2H).

Preparation 40

Compound 32 ($R^3$ = (7-methyl-7-trimethylsilyloxy-1-octyl)

The compound was prepared using the procedure of Preparation 29, but substituting compound 19 for compound 18.

NMR in agreement with structure.

Example 1

1(S),3(R)-Dihydroxy-20(R)-(5'-hydroxy-5'-methyl-1'-hexyloxy)-9,10-seco-pregna-5(Z),7(E),10(19)-triene (Compound 109)

The compound 33 prepared in Preparation 4 (60 mg, 0.11 mmol) was dissolved in ethyl acetate (0.5 ml) and acetonitrile (5 ml) was added. A 5% solution of hydrofluoric acid in acetonitrile/water 8:1 (0.5 ml) was added, and the solution was stirred under nitrogen for 1 hour. Ethyl acetate (50 ml) was added, and the mixture was extracted with saturated aqueous sodium hydrogen carbonate (10 ml) and water (10 ml), dried and evaporated in vacuo. The residue was purified by chromatography (silica gel, ethyl acetate as eluant) to give 109.

NMR: $\delta$ = 0.56 (s, 3H), 1.07 (d, 3H), 1.20 (s, 6H), 1.10–2.05 (m, 24H), 2.15 (bd, 1H), 2.30 (dd, 1H), 2.60 (dd, 1H), 2.72 (m, 1H), 3.20 (m, 2H), 3.57 (m, 1H), 4.21 (m, 1H), 4.42 (m, 1H), 5.00 (bs, 1H), 5.32 (bs, 1H), 5.99 (d, 1H), 6.38 (d, 1H) ppm.

The same compound was obtained when compound 28 (Preparation 25) was used as starting material instead of compound 33.

Example 2

1(S),3(R)-Dihydroxy,20(R)-(2'-hydroxy-3'-methyl-1'-butoxy)-9,10-seco-pregna-5(Z),7(E),10(19)-triene (Compound 101)

A solution of 1(S),3(R)-dihydroxy-20(R)-2'-hydroxy-3'-methyl-1'-butoxy)-9,10-secopregna-5(E),7(E),10(19)-triene (Compound 34) (80 mg) triethylamine (0.2 ml) and anthracene (50 mg) in dichloromethane (8 ml) was illuminated with a radiation from a high pressure ultraviolet lamp (type TQ 150Z; Hanau) for 1 hour. The solution was then filtered and concentrated and the product purified by chromatography (silica gel; ethyl acetate as eluant) to give the title compound. The approx. 1:1 mixture of 2'-epimers obtained from the sequence involving the racemic side chain building block gave the following NMR: $\delta$ = 0.54 and 0.56 (2s, 3H), 0.89 (d, 3H, J=6.8), 0.96 (d, 3H, J=6.8), 1.02–2.10 (m, 19H), 2.30 (m, 1H), 2.58 (m, 1H), 2.82 (m, 1H), 3.10–3.61 (m, 5H), 4.21 (m, 1H), 4.41 (m, 1H), 4.98 (m, 1H), 5.31 (m, 1H), 5.98 (d, 1H, J=11.2), 6.36 (d, 1H, J=11.2).

Example 3

1(S),3(R)-Dihydroxy-20(R)-(3'-hydroxy-3'-methyl-1'-butoxy)-9,10-seco-pregna-5(Z),7(E),10(19)-triene (Compound 102)

A solution of compound 21 (35 mg) in acetonitrile (4 ml) and 40% aqueous hydrofluoric acid (0.2 ml) was stirred at room temperature under nitrogen for 1 hour. Ethyl acetate was added and the mixture was extracted with saturated sodium hydrogen carbonate solution and then brine. The ethyl acetate solution was dried and concentrated in vacuo to give a residue which was purified by chromatography (silica gel, ethyl acetate as eluent) to give the title compound.

NMR: $\delta$ = 0.54 (s, 3H), 1.12 (d, 3H), 1.21 (s, 3H), 1.23 (s, 3H), 1.35–2.20 (m, 17H), 2.30 (dd, 1H), 2.57 (dd, 1H), 2.81 (m, 1H), 3.25 (m, 1H), 3.44 (m, 1H), 3.55 (s, 1H), 3.82 (m, 1H), 4.21 (m, 1H), 4.42 (m, 1H), 4.98 (m, 1H), 5.31 (m, 1H), 5.98 (d, 1H, J=11.3), 6.37 (d, 1H, J=11.3).

Example 4

1(S),3(R)-Dihydroxy-20(R)-(4'-hydroxy-4'-methyl-1'-pentyloxy)-9,10-seco-pregna-5(Z),7(E),10(19)-triene (Compound 105)

Compound 24 prepared in Preparation 16 (128 mg, 0.2 mmol) was dissolved in ethyl acetate (0.2 ml) and acetonitrile (4.4 ml) was added under vigorous stirring. A solution of 5% hydrofluoric acid in acetonitrile/water 8:1 (1.94 ml) was added, and the reaction mixture was stirred under nitrogen at room temperature for 45 minutes. The reaction mixture was worked-up (ethyl acetate) and purified by chromatography (35 g silica gel, 80% ethyl acetate in petroleum ether as eluant) to give the desired compound as a colourless oil.

NMR: $\delta$ = 0.54 (s, 3H), 1.08 (d, 3H), 1.20 (s, 6H), 1.05–2.50 (m, 21H), 2.59 (dd, 1H), 2.81 (bd, 1H), 3.25 (m, 2H), 3.54 (m, 1H), 4.21 (m, 1H), 4.42 (m, 1H), 4.99 (m, 1H), 5.31 (m, 1H), 5.98 (d, 1H, J=11.3), 6.37 (d, 1, J= 11.3) ppm.

Example 5

1(S),3(R)-Dihydroxy-20(R)-(4'-hydroxy-4'-ethyl-1'-hexyloxy)-9,10-seco-pregna-5(Z),7(E),10(19)-triene (Compound 106)

By following the procedure of Example 4 and substituting compound 25 or 26 (Preparation 17 or 27) for compound 24, the desired compound was obtained as a colourless gum.

NMR: $\delta$ = 0.56 (s, 3H), 0.85 (dt, 6H), 1.09 (d, 3H), 1.47 (bq, 1H), 1.00–2.22 (m, 2OH), 2.31 (dd, 1H), 2.61 (bd, 1H), 2.83 (bd, 1H), 3.25 (m, 2H), 3.55 (m, 1H), 4.23 (m, 1H), 4.43 (m, 1H), 5.00 (m, 1H), 5.31 (m, 1H), 6.00 (d, 1H, J=11.3), 6.39 (d, 1H, J=11.3) ppm.

Example 6

1 (S),3(R)-Dihydroxy-20(R)-(5'-hydroxy-5'-ethyl-1'-heptyloxy)-9,10-seco-pregna-5(Z),7(E),10(19)-triene (Compound 110)

Compound 29 prepared in Preparation 24 (40 mg, 0.085 mmol) was dissolved in ethyl acetate (0.1 ml) and acetonitrile (2.3 ml) was added. A solution of 5% hydrofluoric acid in acetonitrile/water 8:1 (1.05 ml) was added, and the reaction mixture was stirred under nitrogen at room temperature for 40 minutes. The reaction mixture was worked-up (ethyl acetate) and purified by chromatography (30 g silica gel, 50% ethyl acetate in petroleum ether as eluant) to give the desired compound.

NMR: $\delta$ =0.56 (s, 3H), 0.85 (t, 6H), 1.08 (d, 3H), 1.45 (q, 4H), 1.02–2.09 (m, 21H), 2.17 (bd, 1H), 2.32 (dd, 1H), 2.60 (dd, 1H), 2.83 (bd, 1H), 3.20 (m, 2H), 3.59 (m, 1H), 4.23 (m, 1H), 4.42 (m, 1H), 5.00 (m, 1H), 5.31 (m, 1H), 6.00 (d, 1H, J=11.3), 6.39 (d, 1H, J=11.3) ppm.

Example 7

1(S),3(R)-Dihydroxy-20(R)-(6'-hydroxy-1'-hexyloxy)-9,10-seco-pregna-5(Z),7(E),10(19)-triene (Compound 111)

Compound 30 prepared in Preparation 23 (233 mg, 0.3 mmol) was dissolved in ethyl acetate (0.6 ml) and acetonitrile (8 ml) was added under vigorous stirring. A solution of 5% hydrofluoric acid in acetonitrile/water 8:1 (4.0 ml) was added, and the reaction mixture was stirred under nitrogen at room temperature for 90 minutes. The reaction mixture was worked-up (ethyl acetate) and purified by chromatography (40 g silica gel, 80% ethyl acetate in petroleum ether as eluant) to give the desired compound as a colourless gum.

NMR: $\delta$ =0.55 (s, 3H), 1.07 (d, 3H), 1.00–2.22 (m, 24H), 2.31 (dd, 1H), 2.60 (dd, 1H), 2.83 (bd, 1H), 3.22 (m, 2H), 3.55 (m, 1H), 3.64 (t, 2H), 4.23 (m, 1H), 4.43 (m, 1H), 5.00 (m, 1H), 5.32 (m, 1H), 6.00 (d, 1H, J=11.3), 6.39 (d, 1H, J=11.3) ppm.

Example 8

1(S),3(R)-Dihydroxy-20(R)-(6'-hydroxy-6'-methyl-1'-heptyloxy)-9,10-seco-pregna-5(Z),7(E),10(19)-triene (Compound 112)

A solution of compound 31 prepared in Preparation 29 (300 mg) and tetrabutylammonium fluoride trihydrate (1.16 g) was stirred under nitrogen at 60° C. for 60 minutes. After cooling, the reaction mixture was worked-up (ethyl acetate) and purified by chromatography (35 g silica gel, 80% ethyl acetate in petroleum ether as eluant) to give the desired compound as a colourless gum.

NMR: $\delta$ =0.55 s, 3H), 1.07 (d, 3H), 1.20 (s, 6H), 1.00–2.22 (m, 24H), 2.30 (dd, 1H), 2.60 (dd, 1H), 2.84 (bd, 1H), 3.22 (m, 1H), 3.55 (m, 1H), 4.22 (m, 1H), 4.43 (m, 1H), 5.00 (m, 1H), 5.32 (m, 1H), 6.00 (d, 1H, 11.3), 6.39 (d, 1H, J=11.3) ppm.

Example 9

1(S),3(R)-Dihydroxy-20(R)-(4'-hydroxy-4'-(1''-propyl)-1'-heptyloxy)-9,10-seco-pregna-5(Z),7(E),10(19)-triene (Compound 107)

The compound was prepared according to the procedure described in Example 4, except that compound 24 prepared in Preparation 16 was substituted with compound 27 prepared in Preparation 34.

NMR: $\delta$ =0.55 (s, 3H), 0.91 (t, 6H), 1.09 (d, 3H), 1.1–2.05 (m, 25H), 2.15 (bd, 1H), 2.32 (dd, 1H), 2.60 (bd, 1H), 2.82 (m, 1H), 3.22 (m, 2H), 3.56 (m, 1H), 4.23 (m, 1H), 4.43 (m, 1H), 5.00 (bs, 1H), 5.32 (bs, 1H), 5.99 (d, 1H), 6.48 (d, 1H) ppm.

Example 10

1(S),3(R)-Dihydroxy-20(R)-(5'-methyl-1'-hexyloxy)-9,10-seco-pregna-5(Z),7(E),10(19)-triene (Compound 108)

The compound was prepared according to the procedure described in Example 4, except that compound 24 prepared in Preparation 16 was substituted with compound 20 prepared in Preparation 35.

NMR: $\delta$ =0.56 (s, 3H), 0.86 (d, 6H), 1.07 (d, 3H), 1.00–2.07 (m, 21H), 2.16 (bd, 1H), 2.31 (dd, 1H), 2.60 (bd, 1H), 2.82 (bd, 1H), 3.20 (m, 2H), 3.55 (m, 1H), 4.23 (m, 1H), 4.43 (m, 1H), 5.00 (bs, 1H), 5.32 (m, 1H), 6.00 (d, 1H, J=11.3), 6.39 (d, 1H, J=11.3) ppm.

Example 11

1(S),3(R)-Dihydroxy-20(R)-(4'-hydroxy-1'-butyloxy)-9,10-seco-pregna-5(Z),7(E),10(19)-triene (Compound 104)

The compound was prepared according to the procedure described in Example 4, except that compound 24 prepared in Preparation 16 was substituted with compound 23 prepared in Preparation 36.

NMR: $\delta$ =0.56 (s, 3H), 1.10 (d, 3H), 1.00–2.20 (m, 19H), 2.32 (dd, 1H), 2.62 (m, 1H), 2.84 (bd, 1H), 3.30 (m, 2H), 3.61 (m, 3H), 4.22 (m, 1H), 4.42 (m, 1H), 5.00 (m, 1H), 5.32 (m, 1H), 6.00 (d, 1H, J=11.3), 6.39 (d, 1H, J=11.3) ppm.

Example 12

1(S),3(R)-Dihydroxy-20(R)-(2'-(1''-hydroxycyclohexyl)ethoxy)-9,10-seco-pregna-5(Z),7(E),10(19)-triene (Compound 103)

The compound was prepared using the procedure of Example 3, but substituting compound 22 for compound 21.

NMR in agreement with structure.

Example 13

1(S),3(R)-Dihydroxy-20(R)-(7'-hydroxy-7'-methyl-1'-octyloxy)-9,10-seco-pregna-5(Z),7(E),10(19)-triene (Compound 113)

The compound was prepared using the procedure of Example 8, but substituting compound 32 for compound 31.

NMR in agreement with structure.

Example 14

Capsule containing Compound 106

106 was dissolved in arachis oil to a final concentration of 1 $\mu$g 106/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 $\mu$l of the 106 in oil solution, such that each capsule contained 0.1 $\mu$g 106.

Example 15

Dermatological Cream Containing Compound 106

In 1 g almond oil was dissolved 0.05 mg 106. To this solution was added 40 g of mineral oil and 20 g of self-emulsifying beeswax. The mixture was heated to liquify. After the addition of 40 ml hot water, the mixture was mixed well. The resulting cream contains approximately 0.5 $\mu$g of 106 per gram of cream.

What we claim is:

1. A compound of the formula I

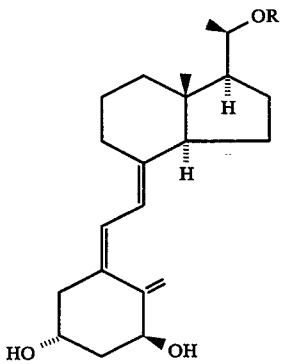

and derivatives of the compounds of formula I in which one or more hydroxy groups have been transformed into —O-acyl or —O-glycosyl or phosphate ester groups, such masked groups being hydrolyzable in vivo, R being a group of formula II

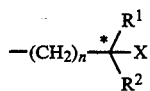

where n is an integer from 1 to 7; $R^1$ and $R^2$, which may be the same or different, stand for hydrogen, $C_1$–$C_5$-alkyl, $C_3$–$C_7$-cycloalkyl, or taken together with the carbon atom (starred in formula II) bearing the group X, $R^1$ and $R^2$ can form a $C_3$–$C_8$ carbocyclic ring; and X stands for hydrogen or hydroxy.

2. A diastereoisomer of a compound according to claim 1, in pure form; or a mixture of diastereoisomers of a compound according to claim 1.

3. A compound according to claim 1, selected from the group consisting of
   a) 1(S),3(R)-Dihydroxy-20(R)-(4'-hydroxy-4'-ethyl-1'-hexyloxy)-9,10-seco-pregna-5(Z),7(E),10(19)-triene
   b) 1(S),3(R)-Dihydroxy-20(R)-(6'-hydroxy-1'-hexyloxy)-9,10-seco-pregna-5(Z),7(E),10(19)-triene
   c) 1(S),3(R)-Dihydroxy-20(R)-(5'-hydroxy-5'-ethyl-1'-heptyloxy)-9,10-seco-pregna-5(Z),7(E),10(19)-triene
   d) 1(S),3(R)-Dihydroxy-20(R)-(5'-hydroxy-5'-methyl-1'-hexyloxy)-9,10-seco-pregna-5(Z),7(E),10(19)-triene
   e) 1(S),3(R)-Dihydroxy-20(R)-(5'-methyl-1'-hexyloxy)-9,10-seco-pregna-5(Z),7(E),10(19)-triene
   f) 1(S),3(R)-Dihydroxy-20(R)-(4'-hydroxy-4'-(1''-propyl)-1'-heptyloxy)-9,10-seco-pregna-5(Z),7(E),10(19)-triene
   g) 1(S),3(R)-Dihydroxy-20(R)-(4'-hydroxy-4'-methyl-1'-pentyloxy)-9,10-seco-pregna-5(Z),7(E),10(19)-triene, and
   h) 1(S),3(R)-Dihydroxy-20(R)-(3'-hydroxy-3'-methyl-1'-butyloxy)-9,10-seco-pregna-5(Z),7(E),10(19)-triene.

4. A pharmaceutical composition containing an effective amount of one or more of the compounds of claim 1, together with a pharmaceutically acceptable, non-toxic carrier therefor.

5. A pharmaceutical composition according to claim 4 in dosage unit form.

6. A dosage unit according to claim 5 containing from 0.05–50 µg of a compound of formula I.

7. A dosage unit according to claim 6 containing from 0.1–25 µg of a compound according to Formula I.

* * * * *